(12) United States Patent
Shfaram et al.

(10) Patent No.: US 7,670,372 B2
(45) Date of Patent: Mar. 2, 2010

(54) SYSTEM AND METHOD FOR BREAST LIFTING

(75) Inventors: Adi Shfaram, Herzliya Pituach (IL); Eyal Gur, Ganei Tikva (IL)

(73) Assignee: MIM-Minimally Invasive Mastopexy Ltd., Kiryat Shmona (IL)

( * ) Notice: Subject to any disclaimer, the term of this patent is extended or adjusted under 35 U.S.C. 154(b) by 1148 days.

(21) Appl. No.: 10/516,685

(22) PCT Filed: Jun. 11, 2003

(86) PCT No.: PCT/IL03/00490

§ 371 (c)(1),
(2), (4) Date: Dec. 6, 2004

(87) PCT Pub. No.: WO03/103536

PCT Pub. Date: Dec. 18, 2003

(65) Prior Publication Data

US 2006/0167338 A1    Jul. 27, 2006

(30) Foreign Application Priority Data

Jun. 11, 2002    (IL) .................................... 150151

(51) Int. Cl.
*A61F 2/12* (2006.01)
(52) U.S. Cl. .......................................... 623/8

(58) Field of Classification Search ................. 623/7, 623/8
See application file for complete search history.

(56) References Cited

U.S. PATENT DOCUMENTS

| 4,372,293 | A | * | 2/1983 | Vijil-Rosales | ............... | 128/898 |
| 5,217,494 | A | | 6/1993 | Coggins et al. | | |
| 5,356,431 | A | | 10/1994 | Pierce | | |
| 5,584,884 | A | | 12/1996 | Pignataro | | |
| 5,676,161 | A | | 10/1997 | Breiner | | |
| 6,960,160 | B2 | * | 11/2005 | Browning | ..................... | 600/37 |

FOREIGN PATENT DOCUMENTS

| EP | 0 230 672 | 8/1987 |
|---|---|---|
| FR | 1.035.202 | 8/1953 |
| FR | 1.035.282 | 8/1953 |
| FR | 2 682 284 | 4/1993 |
| FR | 2 746 298 | 9/1997 |
| WO | 01/39670 A1 | 6/2001 |
| WO | 02/11630 A1 | 2/2002 |

* cited by examiner

*Primary Examiner*—Thomas J Sweet
(74) *Attorney, Agent, or Firm*—The Nath Law Group; Susanne M. Hopkins; Ari G. Zytcer (57) ABSTRACT

A system and a method and a surgical tool for breast lifting, wherein at least one anchor is fixed to a posture tissue, above a desired nipple level, with one or more suspending members suspended from the at least one anchor and extending through the breast for cradling the breast from below.

18 Claims, 9 Drawing Sheets

SYSTEM AND METHOD FOR BREAST LIFTING

FIELD OF THE INVENTION

The present invention is generally in the field of breast shape correction and more specifically it is concerned with breast lifting.

The system according to the present invention may be applied only for the purpose of breast lifting, where the shape of a female's breast is altered or revised, without carrying out a surgery, i.e. only effecting the actual shape of the breasts, without removing breast tissue and without augmentation (adding implants of any type). However, the system may also be applied in conjunction with breast augmentation or breast size reduction, which are surgical procedures.

BACKGROUND OF THE INVENTION

Over the years, factors such as pregnancy, nursing, and the force of gravity take their toll on a woman's breasts. This situation is known as ptosis and is defined as a situation at which the nipple-areola complex projection is lower then the infra-mammary fold, i.e. the nipple is below the level of the lower breast crease. As the skin loses its elasticity, the breasts often lose their shape and firmness and begin to sag, obtaining a teardrop like shape rather then a cone-like shape. Breast lifting, also referred to by the alternative names mastopexy and manzmoplasty, is a procedure used for reshaping saggy and loose breasts, elevating the nipple and areola to a higher level and, thus affording the breast its former shape and firmness which can result in a revitalized body image that can bolster a woman's self-esteem.

Many women use a push-up bra to support their breasts. This however is at times uncomfortable and may be restricting as far as the selection of clothing.

Mastopexy procedure according to prior art techniques involves reducing ptosis (sagging of the breast caused by stretched skin, in many cases due to a great loss of breast tissue). During a breast lift, long incisions are made along the natural creases in the breast and around the dark skin surrounding the nipple (areola), a keyhole-shaped incision above the areola is also made to define the new location for the nipple. Excess skin is removed from the lower section of the breast and the areola, nipple, and underlying breast tissue are repositioned up to a higher position.

The nipple is moved and incisions are closed with sutures.

Several methods for performing a mastopexy are known, and the technique opted for depends mainly on the amount of breast and fat tissue, the amount of skin to be removed, symmetry in volume of breasts and size of areolas, and choice and taste of patient. Since the procedure involves surgery, it may be coupled with breast augmentation and with resizing or repositioning of the areola to a more aesthetically pleasing position and the shape of the mound may be improved by placement of breast implants. Occasionally, only a one-sided breast lift is required, when the other breast is in a reasonable position on the chest and does not require a breast lift.

U.S. Pat. No. 5,676,161 to Breiner discloses a mastopexy procedure according to which an anchor-shaped incision is made, having a bottom line along the infra-mammary crease, using a circular cutter to form the top portion of the incision and an incision around the areola to reduce the diameter thereof. After removing excess skin inside the incision, and breast tissue in the case of mammaplasty, shifting the areola, nipple and underlying breast tissue upward to position the areola/nipple complex within the circular top portion, pulling the flaps of skin formed to the sides of the incision down and around the areola and underneath same, and then suturing adjacent skin edges to complete the lifting and reshaping.

U.S. Pat. No. 5,584,884 to Pignataro discloses a mammary prosthesis comprising a wedge shaped sheet of flexible biocompatible material having reinforced upper and lower attachment portions for attachment to bone of a patient by bone anchors, with the lower attachment portion being anchored to one or more ribs. The lower attachment portion includes a support member less flexible than the sheet material having suture receiving openings for receiving bone anchor sutures.

U.S. Pat. No. 5,217,494 to Coggins et al. discloses a prosthesis for supporting tissue which among others may be used also in a breast lift procedure, wherein one end of the prosthesis is implanted deep into the breast tissue and the opposed end is attached to either the clavicle or the rib.

These procedures are typically performed under general anesthesia, though at times local anesthesia is sufficient, and they may last several hours, depending on the extent of the surgery.

As with any surgery, there is always a possibility of complications such as a reaction to the anesthesia, bleeding and infection (which may cause scars to widen).

Mastopexy does leave noticeable, permanent scars, although are so planned as to be concealed by a woman's bra or bathing suit. One may expect that after about one year the scars will hardly be noticeable. As far as aesthetics, there may also be some dissatisfaction, as the final appearance may not always meet the patient's expectations. Furthermore, a breast lift performed according to conventional techniques won't keep firm forever, the effects of gravity, pregnancy, aging, and weight fluctuations will eventually take their toll again.

It is an aspect of the present invention to provide a novel system and a method for breast lifting, wherein the above drawbacks are significantly reduced or overcome. The system according to the invention and the method for carrying it out are minimally invasive and may be considered as non-surgical, i.e. they do not involve incisions (but rather two or four stab incisions) and removal of excess skin, nor do they require stitches. However, the system may also be used in conjunction with breast enlargement (breast augmentation with mastopexy) or breast size reduction, which are surgical procedures.

SUMMARY OF THE INVENTION

The present invention provides a system for breast lifting, wherein one or more anchors are fixed to a posture tissue, above the desired nipple level with one or more suspending members cradling the breast and extending from the one or more anchors, such that tensioning the suspending members entails lifting of the breast.

The posture tissue is preferably a bone (ribs or collar bone), though it may also be a muscle tissue (pectoral or intercostals). For each breast, anchors may be fixed to one or more posture, depending on the physiology/anatomy of the patient, the shape of the breast prior to lifting, and the desired lifting result. An anchor may be a bolt fixture or a threaded fixture typically, but not restricted thereto, a self tapping screw) for screw-fixation into a bone, a suspending hook for bearing from a bone, i.e. clinging from the bone, or a clasp formed with hooks for grasping soft tissue (muscle). Alternatively, where the posture tissue is a muscle, the suspension member may be fixed thereto by stitching. According to still an alternative, the suspension member may be attached to a bone by tying or yarning it through a bore formed through the bone.

A suspension member according to the invention may be a tendon-like wire or a mesh, made of organic material (e.g. tendons), or synthetic material (e.g. silicone, Gortex, etc.).

According to a preferred embodiment of the invention, the suspension member is formed with or comprises a cradling portion or a cradling member respectively, having increased surface area than the suspension member, for supporting the breast from below and padding it, said cradle being a mesh, a strap or a tube-like member mounted on a wire-like suspension member.

A significant advantage of the present invention, apart from the fact that it is a so called minimal invasive procedure, is that the aesthetic results and appearance may be modified to match with customer's expectations during, or any time after the procedure, i.e. corrections may be easily effected after a while (typically several years), if ptosis reoccurs.

The proposed procedure approves well with other medical procedures and may be combined with breast enlargement (augmentation) or breast reduction.

Even more so, the procedure is completely reversible. Apart from that the procedure is fast and relatively inexpensive, and the patient is dismissed shortly after, leaving practically no scars.

The procedure according to the present invention is carried out by inserting a tool through one or two locations at a bottom face of the breast, directed towards the posture tissue such that it passes through the breast tissue. The tool is used for fixing the anchor to the posture, and according to an embodiment thereof, the tool is also used for guiding and manipulating the suspension member so as to cradle the breast and then tensioning the suspension member at the required extent.

In some cases, depending among others on breast size, two sets of such system may be required for a breast, so as to improve the under support.

According to a further aspect of the present invention there is provided a method for breast lift, said method comprises the following steps: a) introducing through the breast at least one anchor and fixing it to a posture tissue; b) yarning a suspension member through the breast; said suspension member extending from said at least one anchor and passing within fat tissue at a bottom portion of the breast so as to cradle the breast; c) tensioning the suspension member to thereby lift the breast; and d) fixating the length of the suspension member.

An alternative method comprises the following steps: a) yarning a cradling member of a suspension member through the breast, at a bottom thereof, such that loose ends thereof extend from the breast; b) fixing at least one anchor to a posture tissue, at a level above the desired nipple level; c) attaching a suspension member to the at least one anchor; d) articulating the loose ends of the cradling member to the suspension member and fixedly adjusting the length thereof.

According to a preferred embodiment, two anchors are fixed to the posture tissue, with a suspension member extending from each one, such that the loose ends of the cradling member are articulated to each respective end of a suspension member. Still preferably, excessive ends of the suspension members and of the cradling member, are trimmed.

The method according to an embodiment thereof further comprises fitting a cradle member on the suspension member, for supporting the breast from below. According to one application, the cradle member is a strap-like portion (possibly a mesh-like material) continuously extending from the suspension member.

According to a different application, the cradle member is integral with or mounted over a supplementary member fixedly attached to the suspension member, whereby the breast height is set by adjusting the relative length of the suspension member and the supplementary member.

Where the system is used in conjunction with a breast enlarging procedure, the cradling portion may directly support the implant.

The present invention has several significant advantages, namely: a) the mere incisions are two or four stab incision, which are fast healing and practically leave no scars; b) the procedure is considerably shorter than any prior art procedure; c) the procedure may be carried out under local anesthesia, whereby the patient may be dismissed shortly after; d) the procedure is adjustable and reversible at any time; e) the procedure is considerably cheaper then any prior art procedure; and f) the procedure does not affect sensitivity of the breast or nipple and it does not have any consequences concerning breast feeding.

For carrying out the procedure of the present invention, there is provided a tool kit, which depending on the specific procedure, will include one or more of the following tools: a) tool for stabbing the breast and yarning a cradling member there through, such that its free ends extend from the breast; the same tool may be used for creating a passage through the breast for the suspension member; b) tool for deploying and fixing the anchors to a posture tissue (bolting or screwing in the case of a bone posture; stitching in the case of muscle tissue); this tool is also used for yarning the suspension member which is articulated to the anchor; c) tool for articulating and tensioning ends of the cradling member to the suspension members, and for adjusting the length, fixating and trimming excessive ends.

However, according to different applications, rather than using a tool, the slack end of the cradling member and the corresponding slack end of the suspension member, may be manually tensioned and tied to one another, their ends being trimmed by conventional means.

The present invention further calls for a tool useful in carrying out a procedure according to the invention, said tool adapted for tensioning and clamping cord-like slack ends of the cradling member and a corresponding suspension member; said tool comprising a housing fitted at a fore end with a cord receiving opening for receiving two or more cords, a clamp deploying mechanism for clampingly articulating the at least two cords, and a cord trimming mechanism for trimming the cords adjacent the clamp.

According to another aspect of the present invention, there is provided a kit for performing a breast-lift procedure, the kit comprising at least one set of suspension members, anchoring means for anchoring a suspension member to a posture tissue, and means for tensioning and fixating the suspension member. The kit may also comprise one or more breast-cradling/padding members and one or more tools, e.g. a tool to facilitate tensioning clamping and trimming of a suspension member and a cradling member.

BRIEF DESCRIPTION OF THE DRAWINGS

In order to understand the invention and to see how it may be carried out in practice, some embodiments will now be described, by way of non-limiting examples only, with reference to the accompanying drawings, in which.

DETAILED DESCRIPTION OF EMBODIMENTS

Figure 1:
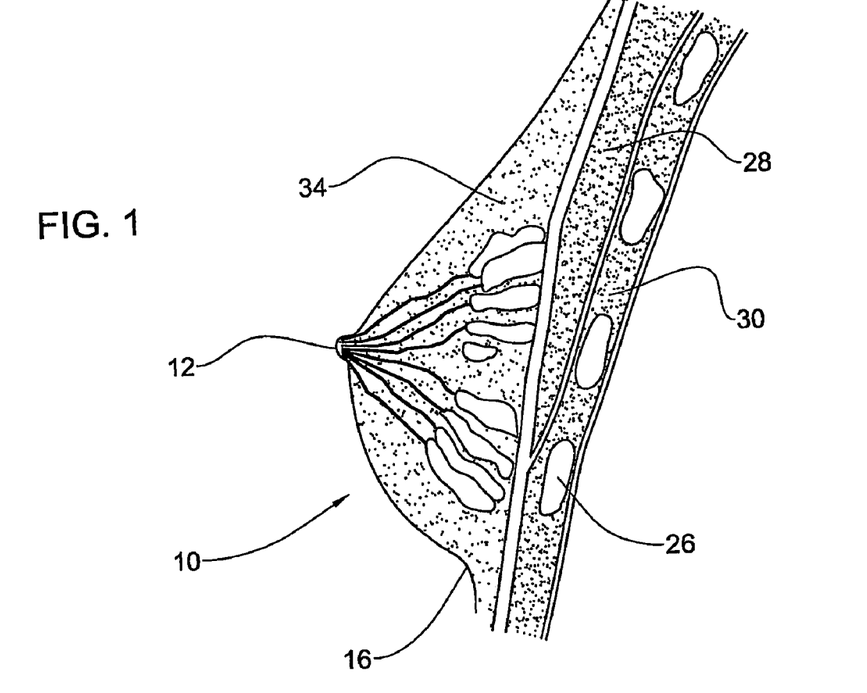
FIG. 1 is a partially sectioned side view illustrating the anatomy of an erect, firm breast.
Figure 2:
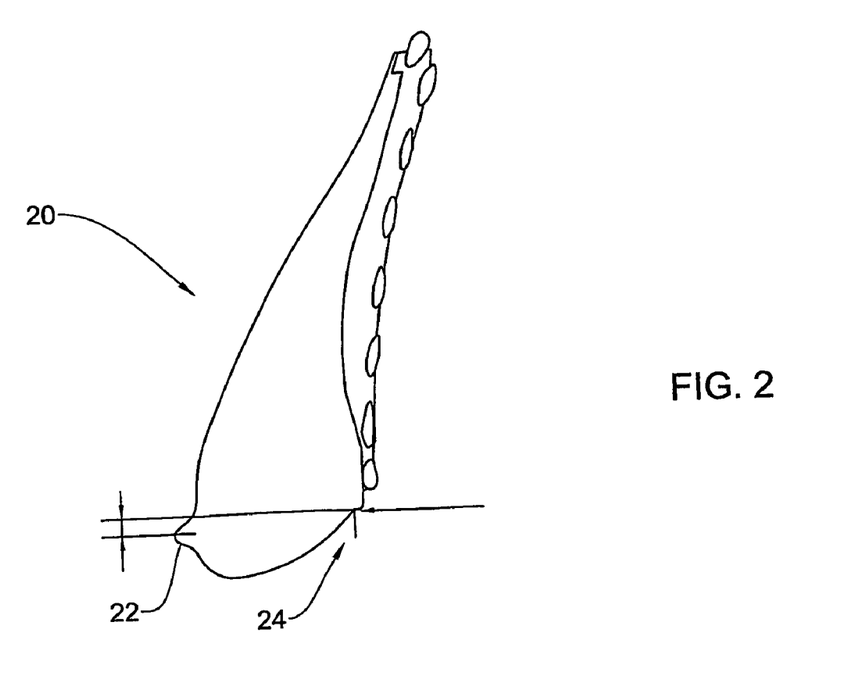
FIG. 2 is a side view illustrating a saggy breast.

The breast 10 seen in FIG. 1 is firm and erect though of small size. One can notice that the nipple 12 is facing forward and that the nipple-areola complex projection is higher than the infra-mammary fold 16, i.e. the nipple 12 is well above the level of the lower breast crease 16. Contrary thereto, the breast 20 of FIG. 2 is saggy and it is noticed that the nipple 22 is facing downward and extends below the infra-mammary fold 24.

Reverting to FIG. 1, one can further notice several ribs 26, pectoral muscle 28, intercostals muscles 30 and the fat tissue 34.

Turning now to FIGS. 3A to 3H, there is illustrated a sequence of carrying out a breast lift according to a first embodiment of the present invention.

Figure 3A:
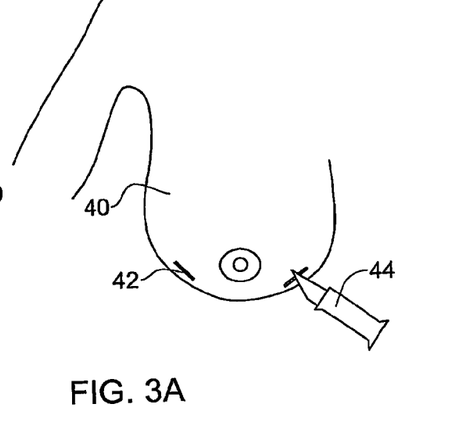
FIGS. 3A to 3H are consecutive steps of carrying out a breast lift procedure according to a first embodiment of the present invention.
Figure 3B:
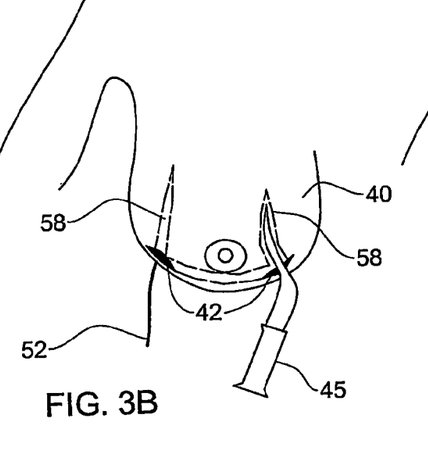
Figure 3C:
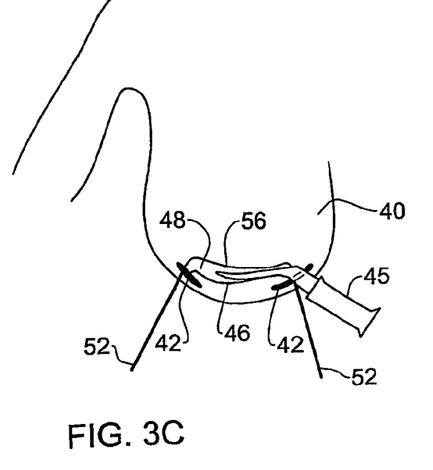
Figure 3D:
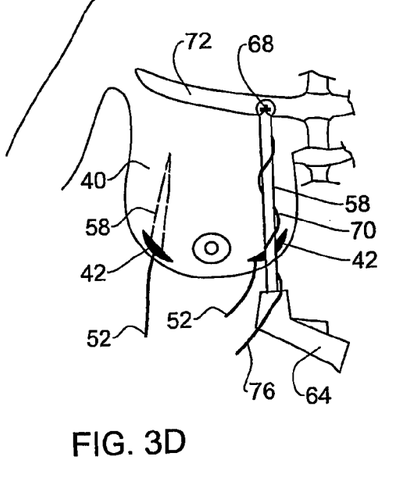

At a first step, after locally anesthesia of the beast 40, two stab incisions 42 are formed at a bottom portion of the breast, with a surgical tool 44 (FIG. 3A). Then using another tool 45, a passage 46 is formed between the incisions and using that tool, a cradling member 48 is yarned through the passage 46, such that its slack ends 52 extend through the incisions 42 (FIG. 3B). As seen in FIG. 3B, the cradling member 48 comprises a central band-like portion 56 adapted for cradling and supporting the breast from below, and two yarns 52 extending at each side thereof.

The band-like portion 56 as well as the yarns 52 may be made of organic material, e.g. tendons, or synthetic material e.g. Gortex, etc.

Using tool 45, two passages 58 are made (FIG. 3C), preferably extending from the incisions 42. It is however noticed that the passages 58 may be formed before inserting the cradling member 48. Through the passages 58 an anchoring tool 64 is applied (FIG. 3D), said tool 64 being pre-fitted with an anchoring screw 68 (preferably a self tapping screw) and a suspension member in the form of a cord 70 attached to the anchor screw 68. By means of tool 64 the anchor screw 68 is screwed to rib 72. The same procedure takes place through both passages 58, with slack ends 76 of the suspension members extending from the incisions 42.

Figure 3E:
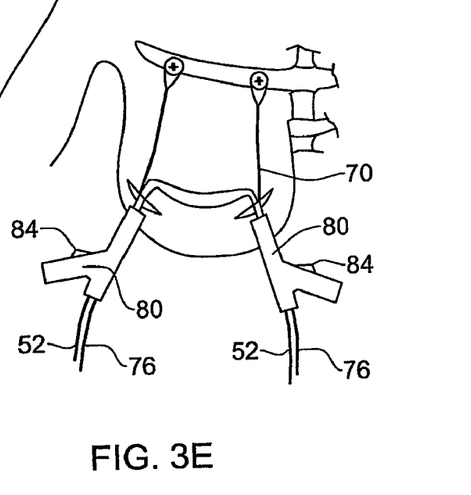
Figure 3F:
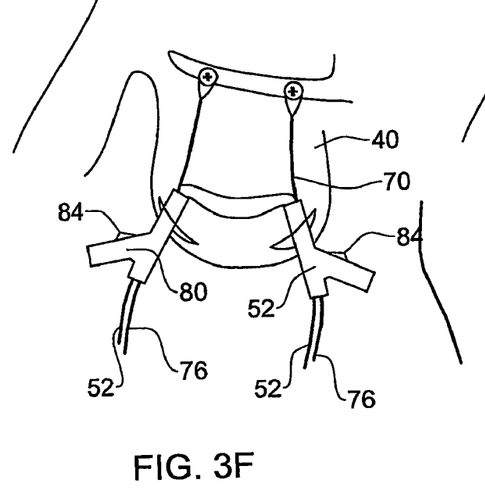

Using a different tool designated 80 (such a tool is disclosed in more detail with reference to FIGS. 8A to 8D), slack end 52 of the cradling member and the corresponding slack end 76 of the suspension member, are articulated, simultaneously at both sides of the breast (FIG. 3E). Preferably while the patient is in an upright position, tensioning begins using the tool 80, by repeatedly pulling trigger 84, until the breast elevates to a desired position. This action provides real time indication of the breast's new form and position, and even more so, the patient may take part in deciding to what extent to lift the breasts.

Figure 3G:
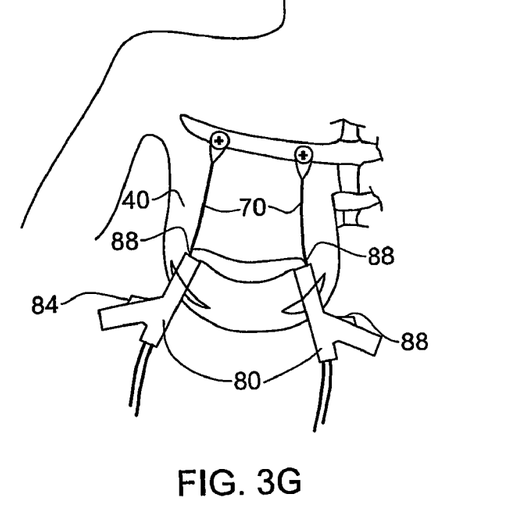
Figure 3H:
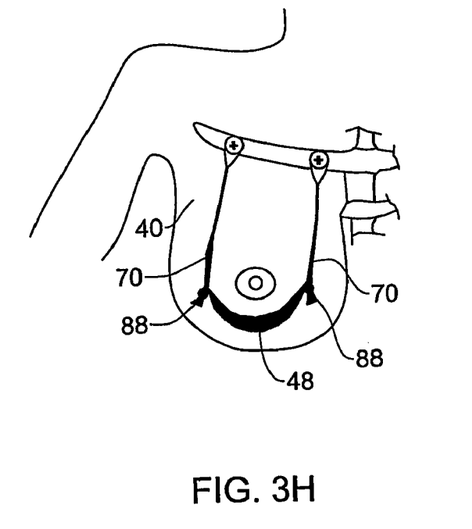

Once the breast 40 assumes the desired repositioning and form, a fixing clamp 88 is applied by tool 80 (FIG. 3G), and by further manipulating trigger 84 of the tool 80, the slack ends 52 of the cradling member and the corresponding slack ends 76 of the suspension member are trimmed (FIG. 3H).

The tool is then removed and shortly after the patient may be dismissed, with complete healing expected in a matter of days, essentially not leaving any noticeable scars.

According to a different application, rather than using a tool, the slack end 52 of the cradling member and the corresponding slack end 76 of the suspension member may be manually tensioned and tied to one another, their ends being trimmed by conventional means, as known in the art of suturing.

Figure 4A:
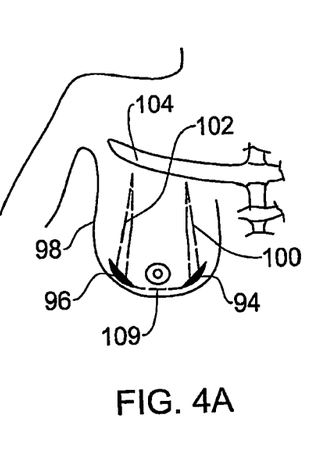
FIGS. 4A to 4G are consecutive steps of carrying out a breast lift procedure according to a second embodiment of the present invention.
Figure 4B:
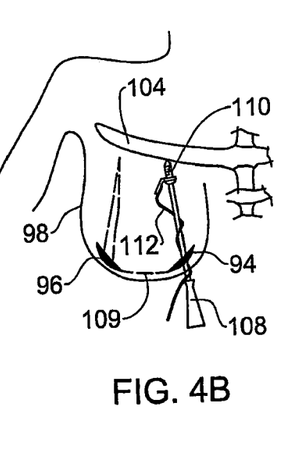

Further attention is now directed to FIGS. 4A to 4Q illustrating still another method for carrying out a breast lift according to the present invention.

Figure 4C:
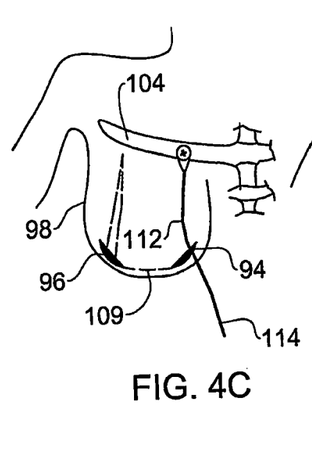

First, two stab incisions 94 and 96 are made at a bottom portion of the breast 98, and a corresponding passage 100 and 102 is formed extending towards a suitable posture tissue, rib 104 in the present example (FIG. 4A). A transverse passage 109 is formed between the incisions 94 and 96. Then a tool 108, resembling a screwdriver, is introduced through the first passage 100, said tool carrying at its fore end an anchor in the form of screw 110, to which a suspension cord 112 is attached. The anchor is fixed to the rib 104 (FIG. 4B), and the tool 108 is removed leaving a long free end 114 of the suspension member, extending from the incision 94 (FIG. 4C). Preferably, tool 108 is fitted with a screw holding member (not shown), to prevent the screw 110 from departing from the tip of the tool.

Figure 4D:
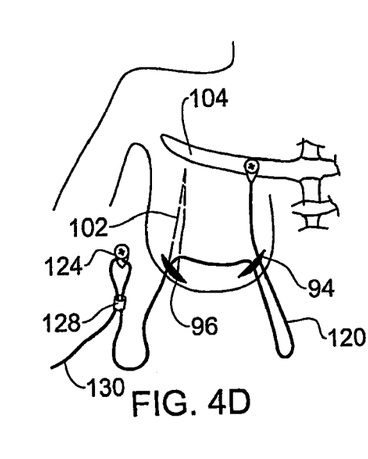
Figure 4E:
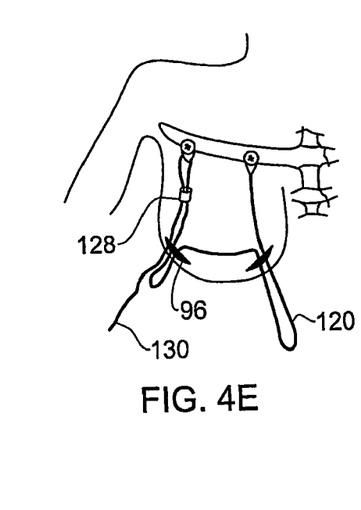
Figure 4F:
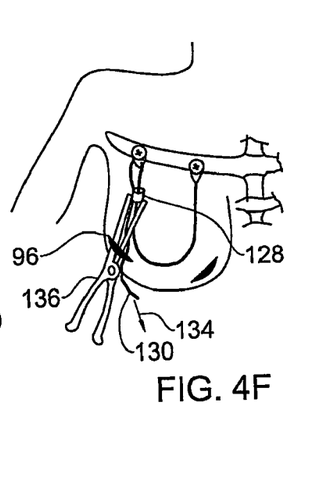
Figure 4G:
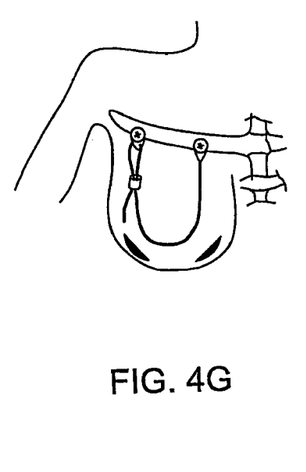

The free end 114 is then yarned back through the incision 94, through the transverse passage 109 and out through the second incision 96, leaving a looped portion 120 extending from the first incision 94 (FIG. 4D). A second anchor 124 is then provided, which comprises an eye for slidingly receiving the suspension cord 112, and a clamp 128 is loosely mounted over two overlapping portions of the suspension cord (FIG. 4D). Using the same tool 108 (not shown in FIG. 4D), the second anchor 124 is introduced through the second passage 102 and is then attached to the rib 104, whilst the loose end 130 of the suspension cord extends from incision 96 (FIG. 4E).

The loose end 130 is then pulled in direction of arrow 134 (FIG. 4F), shrinking the looped portion 120 and tensioning the suspension cord until the breast is deformed and lifted to a desired extent. At this point, a clamping tool 136 is introduced through incision 96, to shrink the clamp 128, so as to thereby fixate the tension of the suspension cord.

As mentioned in connection with the embodiment of FIG. 3, the tensioning step (FIG. 4F) is preferably carried out while the patient is in an upright position, such that actual indication is available regarding the breast's new form and position, and even more so, the patient may take part in deciding to what extent to lift the breasts.

The loose end 130 is then trimmed, possibly by tool 136 (FIG. 4G) and the procedure is complete. Shortly after the patient may be dismissed, with complete healing expected in a matter of days, essentially not leaving any noticeable scars.

Figure 5A:
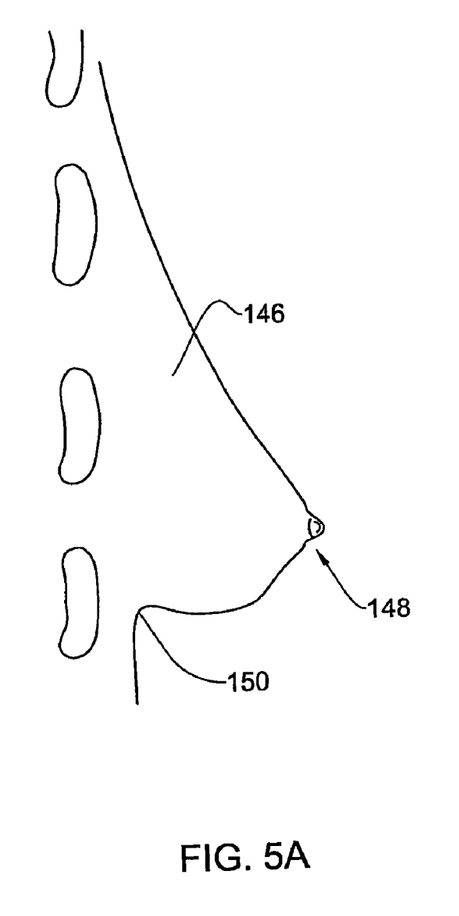
FIG. 5A is a side section through a saggy breast prior to breast lift.
Figure 5B:
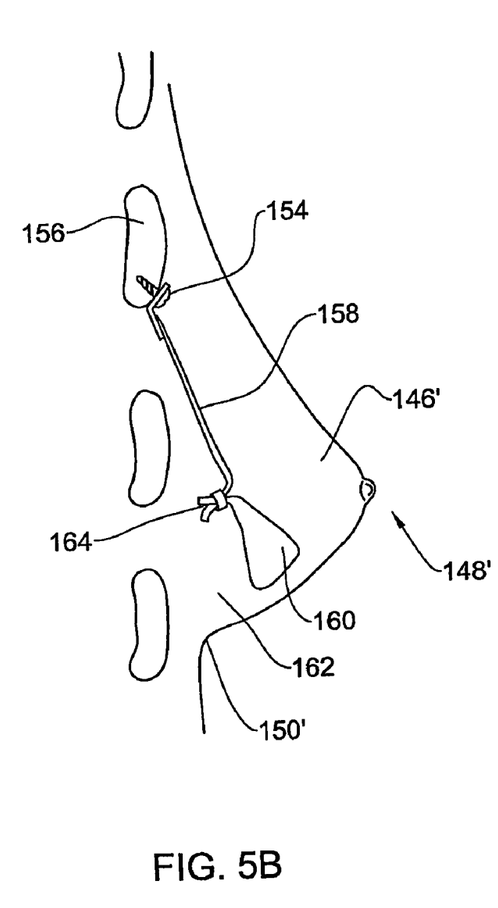
FIG. 5B is a side section through the breast in FIG. 5A, after breast lift.

Turning now to FIGS. 5A and 5B, there is illustrated a breast 146 which in FIG. 5A is prior to beast lift and it is noticeable that nipple-areola complex 148 projection is lower then the infra-mammary fold 150. However, in FIG. 5B the same breast, now designated 146' has undergone a breast lift procedure in accordance with the present invention and in this Figure the nipple-areola complex 148' projection is higher then the infra-mammary fold 150'. Further noted in FIG. 5A, a screw type anchor 154 is screw fixed into a rib 156, with a suspension member in the form of cord 158 being attached thereto. A cradling member 160 extends through the fat tissue 162 of the breast, supports the breast from below, said cradling member being tensioned and articulated to the suspension member by clamp 164, thus lifting the breast and imparting it a firm and erect appearance.

Figure 6:
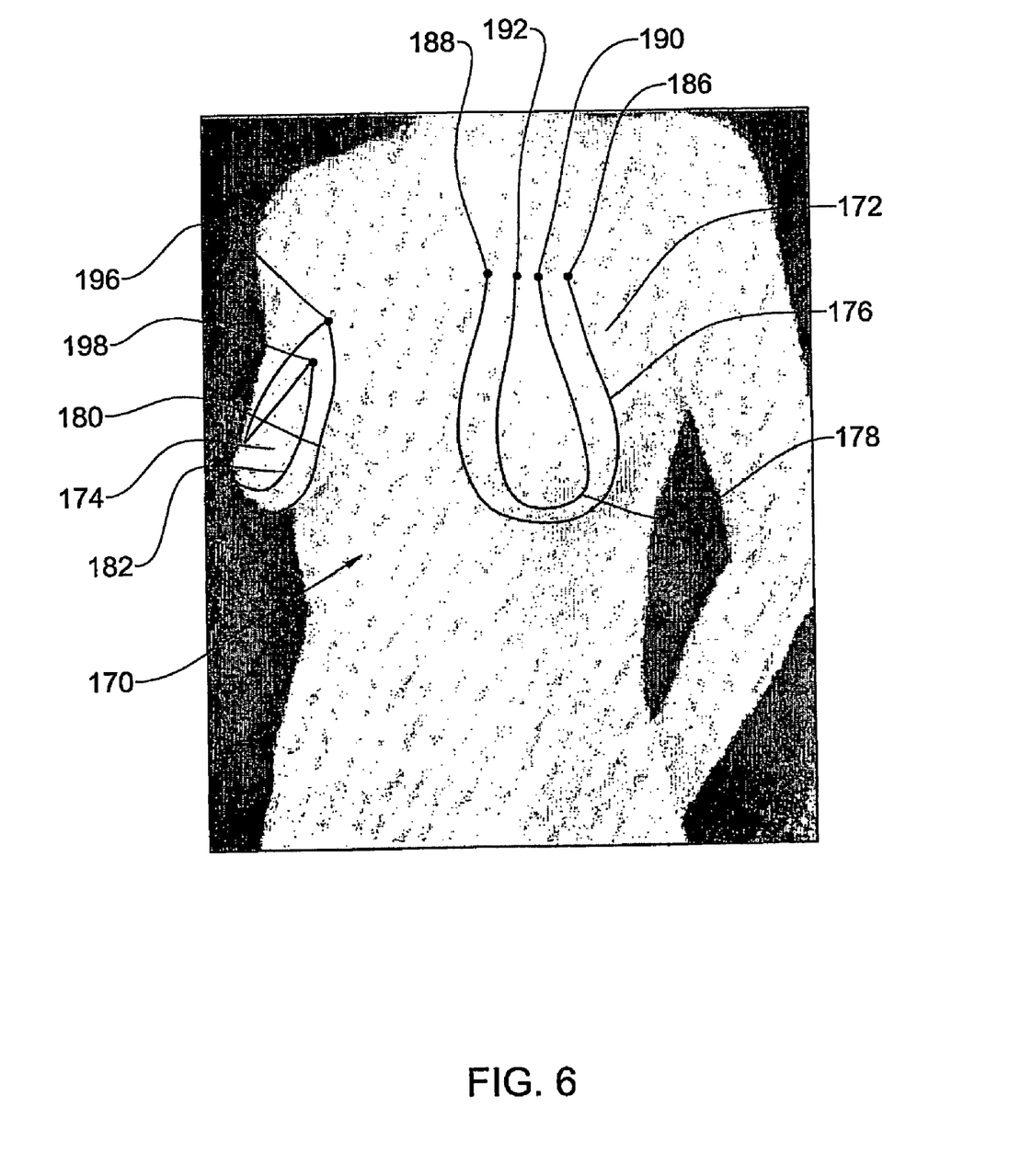
FIG. 6 is a front view of a female body, superimposing how the breasts are supported by two suspension members.

In FIG. 6, a female's thorax 170 is seen in which both the left and right breast 172 and 174 respectively, are supported by two sets of breast-lifting systems (176 and 178 for the right breast; and 180 and 182 for the left breast), each breast-lifting system being substantially similar to the systems disclosed herein above. The difference resides in that each breast is supported by two sets and it is noticed that whilst in the left breast 172 each suspension member is anchored by two distinct anchors (186; 188 for breast-lifting system 176, and 190; 192 for breast-lifting system 178), in the right breast 174 each suspension member is anchored by only one, common anchor (196 for breast-lifting system 180, and 198 for breast-lifting system 182).

Figure 7A:
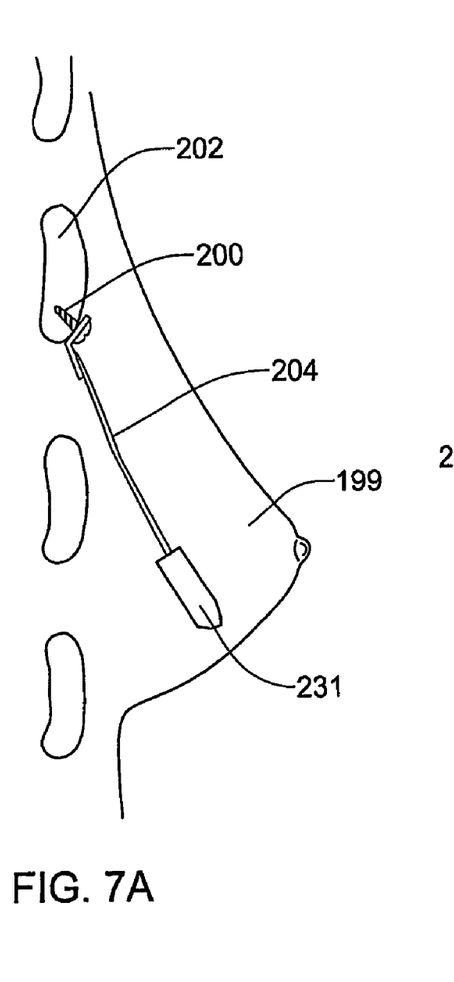
FIGS. 7A to 7C are schematic side views illustrating different embodiments of anchoring means.
Figure 7B:
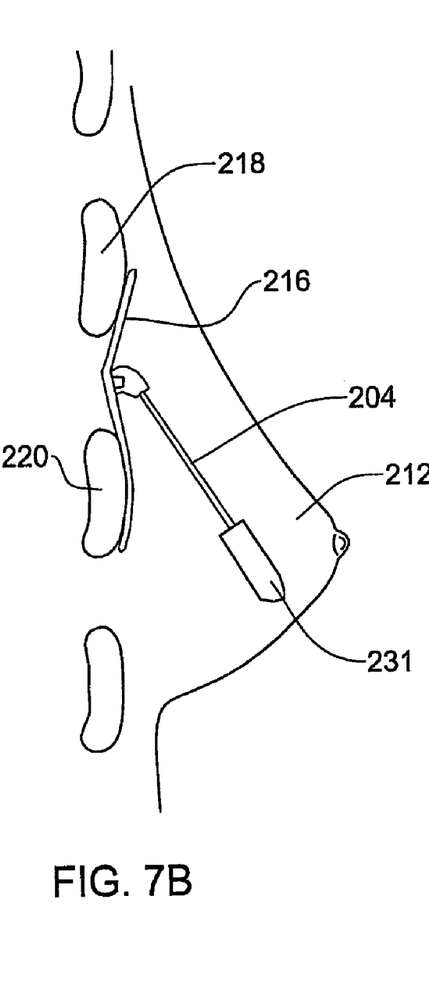
Figure 7C:
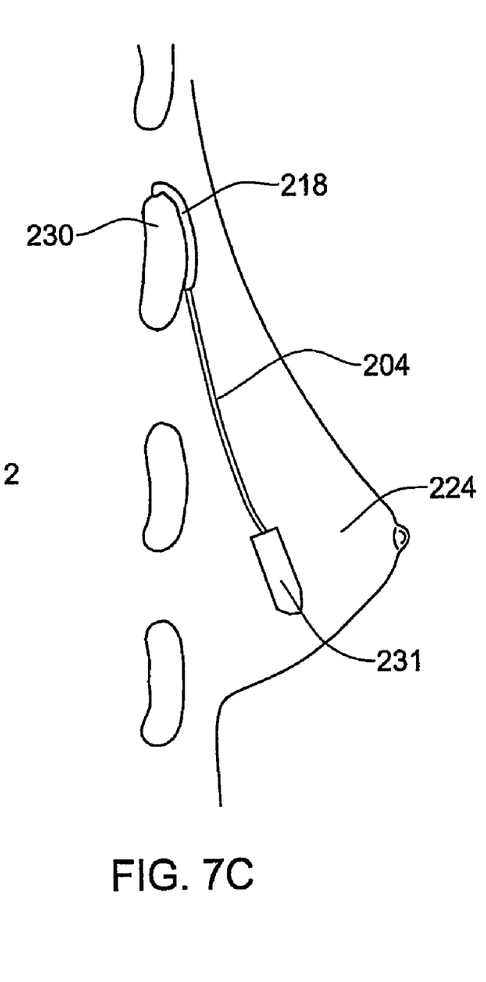

FIGS. 7A to 7C illustrate 3 breasts, each lifted by a breast lifting system according to the invention, each fitted with a different anchoring means for attaching the suspension member to a posture tissue. In the breast 199 of FIG. 7A, the anchor is a threaded anchor 200 screw-coupled into a rib 202, with a suspension member 204 attached to the anchor. It is appreciated that the screw-type anchor may be a self-screwing thread type i.e. does not require preparatory boring in the bone tissue, there may be a bolt-type anchor, i.e. of the type which is inserted into a bore pre-drilled in the rib.

The breast 212 in FIG. 7B is supported by a system in which a brace-type anchor 216 which is attached to two neighboring ribs 218 and 220, e.g. by screws etc. in FIG. 7C the breast 224 is supported by a system according to the invention in which the anchor is a suspending hook 228 bearing (clinging) from rib 230. However, as mentioned herein above, the anchoring member may also be attached to muscles e.g. by stitching or by a clasp, etc.

The cradling member 231 illustrated in the FIGS. 7A to 7C may be, for example, a tube-like member mounted on the suspension member 204, for increasing the sectional area thereof.

According to another aspect of the invention, there is provided a surgical tool useful in carrying out the method disclosed with reference to FIGS. 3A to 3H. A tool 250 is illustrated in more detail with further reference to FIGS. 8A to 8D.

Figure 8A:
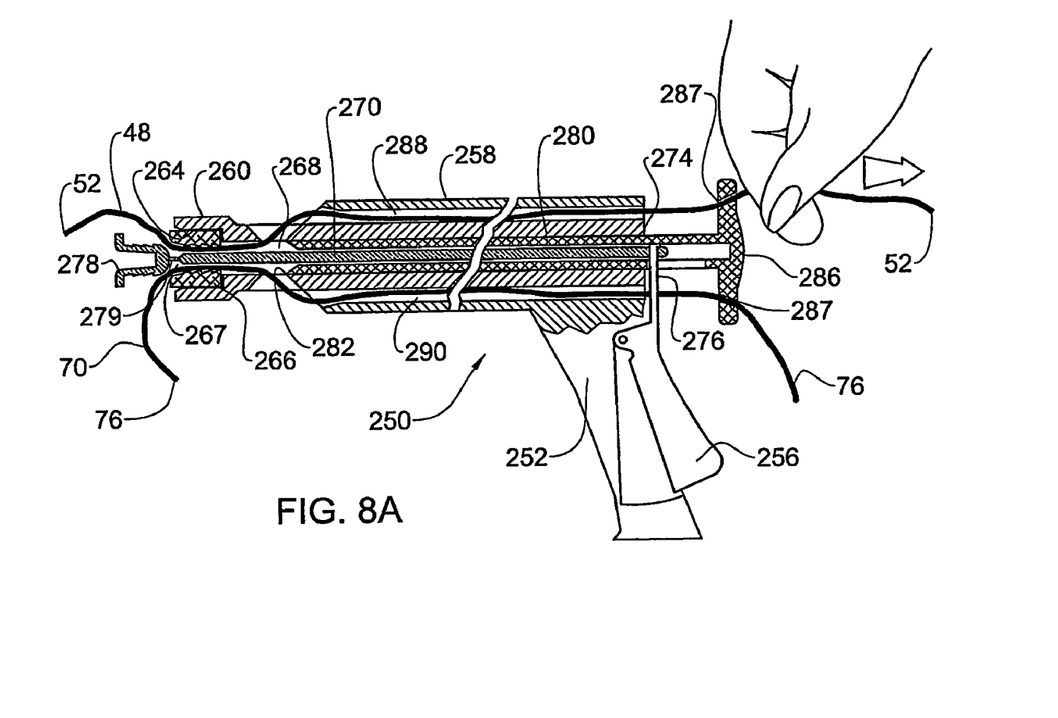
FIGS. 8A to 8D illustrate a surgical tool useful in carrying out a breast-lifting procedure, in four consecutive operative positions.
Figure 8B:
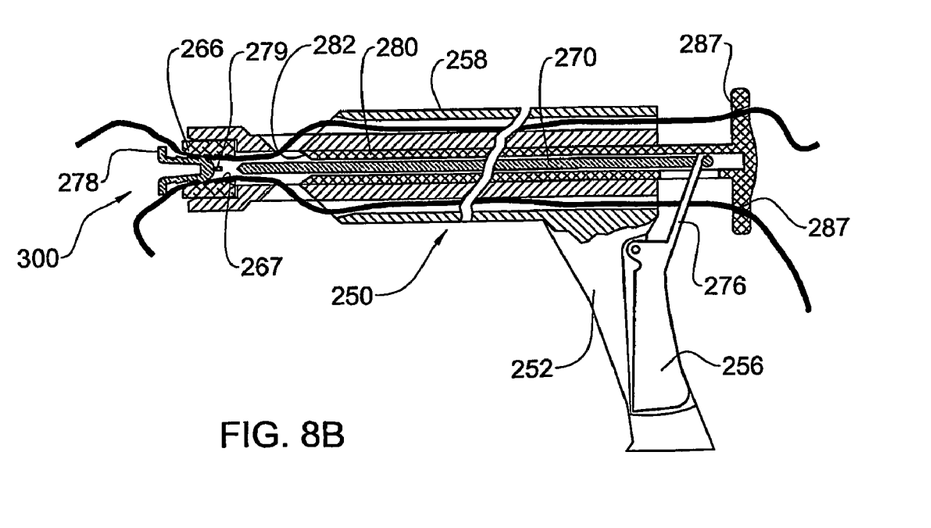

The tool 250 has a general pistol-like shape having a gripping portion 252 fitted with a clamping trigger 256, and a stem portion 258 having a fore end 260.

At least the fore end is sized for inserting through a stab-incision formed in a breast, as illustrated for example in FIGS. 3E to 3G. The fore end 260 is fitted with a clamping unit receptacle 264 (best seen in FIG. 8D), accommodating an annular locking member 266 having a serrated inner bore 267 sized to receive therethrough an end of the cradling member 52 and a corresponding end of the suspension member 76 (see FIG. 3E). The stem portion 258 comprises a central bore 268 accommodating an elongate plug-stem 270 extending from the clamping unit receptacle 264 towards a rear end 272 of the stem portion, where it projects and is articulated to a lever 276 of the trigger 256. A plug 278 is integrally connected by a tear zone 279 to a fore end of the plug-stem 270. The plug 278 is serrated and sized for snapingly locking within the locking member 266.

Coaxially received within the central bore 268 there is a trimmer 280 having a trimming end 282 at a fore end and a pusher 286 at its rear end, said pusher comprising two bores 287. Two bores 288 and 290 extend through a portion of the stem portion 258, fitted for receiving the end of the cradling member 52 and a corresponding end of the suspension member 76.

In use, the end of the cradling member 52 and the suspension member 76 are threaded through the locking member 266, yarned through the bores 288 and 290 respectively, then extending through the rear end 274 and through the bores 287 (FIG. 8A). This step is carried out at a step corresponding with the step illustrated in FIG. 3E. Then, the ends of the cradling member 52 and of the suspension member 76 are manually tensioned (FIG. 8A) to the desired position of the breast. Upon squeezing trigger 256 (FIG. 8B) the plug-stem 270 is axially displaced in a rear direction, forcing the plug 278 to engage with the locking member 266, clamping therebetween the cradling member 52 and the suspension member 76, at their tensioned position. Further squeezing of trigger 256 entails rupture of the tear zone 279 giving rise to a clamping unit 300 consisting of the plug 278 and the locking member 266.

Figure 8C:
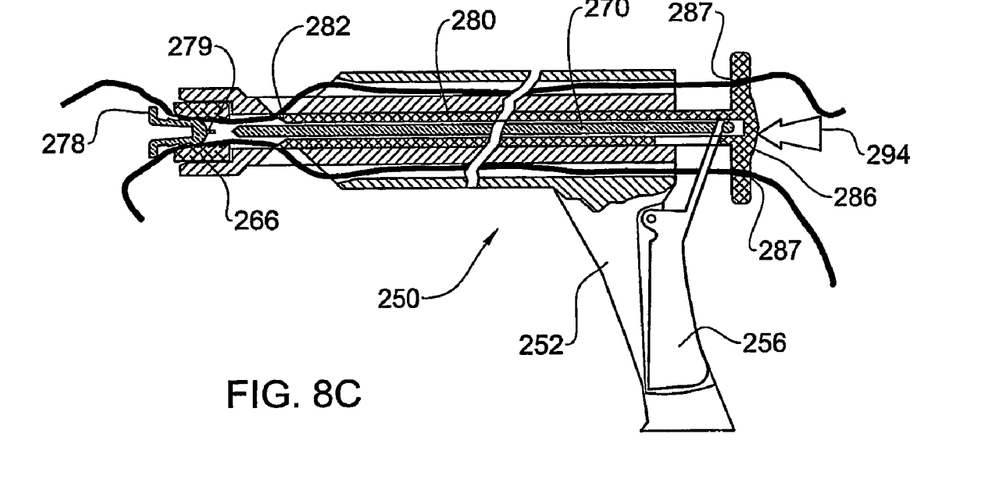
Figure 8D:
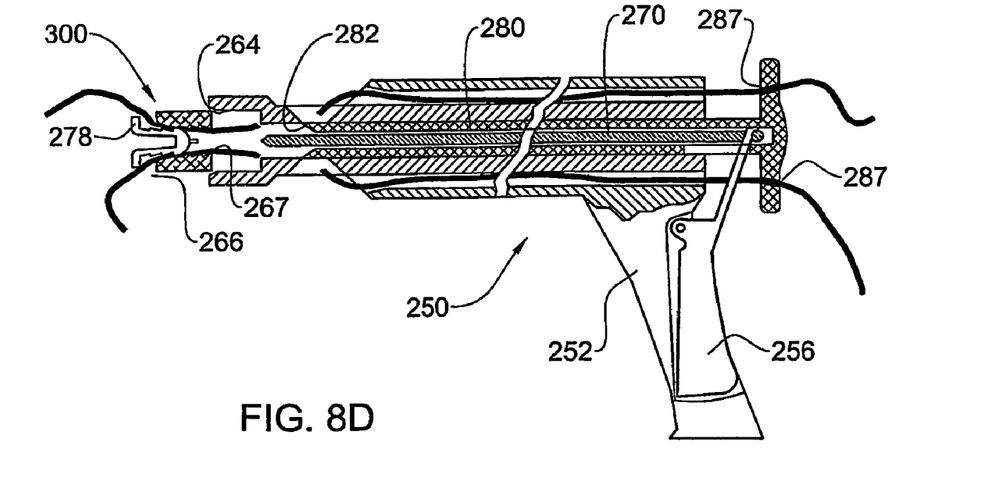

Then, pusher 286 is axially pressed in a forward direction as illustrated by arrow 294, entailing the trimming end 282 to shear the cradling member 52 and of the suspension member 76 (FIG. 8C). The tool may now be removed, discharging the clamping unit 300 and leaving it within the breast (not shown).

The tool 250 may be disposable or, according to a different embodiment may be made of a material suitable for reuse (after sterilization), where spare plugs (and their associated plug-stems) are provided.

Whilst some embodiments have been described and illustrated with reference to some drawings, it will be appreciated that many changes may be made therein without departing from the general spirit and scope of the invention, mutatis, mutandis.

The invention claimed is:

1. A system for minimally invasive breast lifting and imparting a breast with natural and lifted shape, the system comprising:
   one or more anchors adapted to be fixed to a posture tissue above a desired nipple level;
   two or more readily adjustable suspension members suspended from the one or more anchors each readily adjustable suspension member having a free end; and
   a cradling portion having a first end and a second end and being configured to cradle the breast from below, the first end and the second end of the cradling portion being integral with and/or movably attached to the free end of a respective suspension member, and the cradling portion having a width greater than the width of each of the two or more readily adjustable suspension members,
      wherein the system is configured to lift and thereby impart the breast with a natural shape.

2. The system according to claim 1, wherein the cradling portion is a mesh-like portion.

3. A system according to claim 1, wherein the anchor is a bolt fixture or a threaded fixture fixed to a rib or a collar bone.

4. A system according to claim 3, wherein the anchor is a self tapping screw.

5. A system according to claim 1, wherein the anchor is a stitching to a muscle.

6. A system according to claim 1, wherein the anchor is a clasp for clasping a muscle.

7. The system according to claim 1, wherein the anchor is a suspending hook bearing or clinging from a rib.

8. The system according to claim 1, wherein the suspension member and the cradling portion comprise one or more organic or inorganic materials.

9. A system according to claim 8, wherein the suspension member and the cradling portion are made of tendons.

10. The system according to claim 1, comprising two suspension members.

11. The system according to claim 10, wherein the free end of each suspension member is attached to a corresponding anchor.

12. The system according to claim 10, wherein both free ends of the suspension members are attached to a single anchor.

13. The system according to claim 1, wherein the one or more anchors and the two or more suspension members are deployable in a non-operable procedure.

14. The system according to claim 13, wherein the one or more anchors and the two or more suspension members are deployable through stab-incisions formed at a bottom surface of the breast.

15. The system according to claim 1, being removable at any time.

16. The system according to claim 1, wherein the first end and the second end of the cradling portion are fixedly attached to a free end of a respective suspension member.

17. A system for minimally invasive breast lifting and imparting a breast with natural and lifted shape, the system comprising:
one or more anchors adapted to be fixed to a posture tissue above a desired nipple level;
two or more readily adjustable suspension members having
an anchoring end, and
a cradling end,
the two or more readily adjustable suspension members being suspended from the one or more anchors at the anchoring end and being movably attached or fixed to the one or more anchors;
a cradling portion having
a first end movably attached to and/or integral with the cradling end of one of the two or more readily adjustable suspension members, and
a second end movably attached to and/or integral with the cradling end of one of the two or more readily adjustable suspension members
the cradling portion being configured to cradle the breast from below and the cradling portion having a width greater than the width of each of the two or more readily adjustable suspension members
wherein the system is configured to lift and thereby impart the breast with a natural shape.

18. A system for minimally invasive breast lifting and imparting a breast with natural and lifted shape, the system comprising:
one or more anchors adapted to be fixed to a posture tissue above a desired nipple level;
at least one readily adjustable suspension members having
at least one an anchoring point, and
at least one a cradling point,
the at least one readily adjustable suspension members being suspended from the one or more anchors at the at least one anchoring point and being movably attached to and/or integral with the one or more anchors;
a cradling portion having
a first end movably attached to and/or integral with the at least one cradling point of one of the at least one readily adjustable suspension members, and
a second end movably attached to and/or integral with the cradling end of one of the at least one readily adjustable suspension members
the cradling portion being configured to cradle the breast from below and the cradling portion having a width greater than the width of each of the two or more readily adjustable suspension members,
wherein the system is configured to lift and thereby impart the breast with a natural shape.

* * * * *